Figure 1:
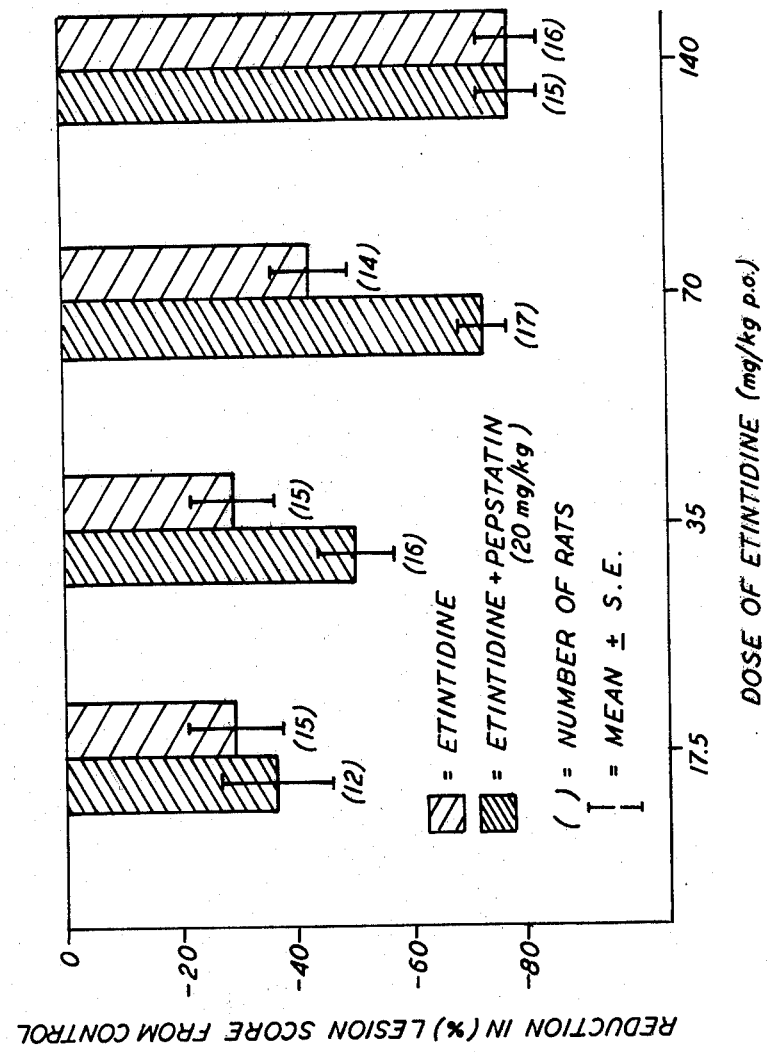

United States Patent [19]  [11]  4,339,439
Buyniski et al.  [45]  Jul. 13, 1982

[54] PHARMACEUTICAL METHODS AND COMPOSITIONS

[75] Inventors: Joseph P. Buyniski, Syracuse; Robert L. Cavanagh, Manlius; Maxwell Gordon, Syracuse, all of N.Y.

[73] Assignee: Bristol-Myers Company, New York, N.Y.

[21] Appl. No.: 225,945

[22] Filed: Jan. 19, 1981

[51] Int. Cl.$^3$ ............................................. A61K 37/00
[52] U.S. Cl. ..................................................... 424/177
[58] Field of Search ......................................... 424/177

[56] References Cited

U.S. PATENT DOCUMENTS 4,101,650  7/1978  Umezawa ............................. 424/44
4,112,234  9/1978  Crenshaw et al. ............... 424/273 R

OTHER PUBLICATIONS

Myers et al., Clinical Research, 28, 30A 1980.
Umezawa et al., J. Antibiotics 23, 259–262, 1970.
Bonnevie et al., Gut, 20, 624–628 (1979).
Svendsen et al., Scand. J. Gastroent. 14, 929–932 (1979).
Strauss et al., Surg. Forum 28, 361–363, 1977.
Dajani et al., J. Pharmacol. Exp. Ther., 210, 373–377, (1979).
British Medical Journal 95–96, (1980).

Primary Examiner—Delbert R. Phillips
Attorney, Agent, or Firm—Richard R. Lloyd

[57] ABSTRACT

Enhanced antiulcer activity is obtained in warm-blooded animals by the concomitant administration of the histamine $H_2$-receptor antagonist, etintidine, and the pepsin complexing agent, pepstatin. Concomitant administration of the two entities reduces the amount of etintidine necessary for effective treatment, thereby decreasing its side effect liability.

17 Claims, 2 Drawing Figures

COMPARATIVE EFFECTS OF ETINTIDINE AND COMBINATIONS OF ETINTIDINE AND PEPSTATIN IN THE PREVENTION OF HCl-INDUCED GASTRIC EROSIONS IN THE RAT.

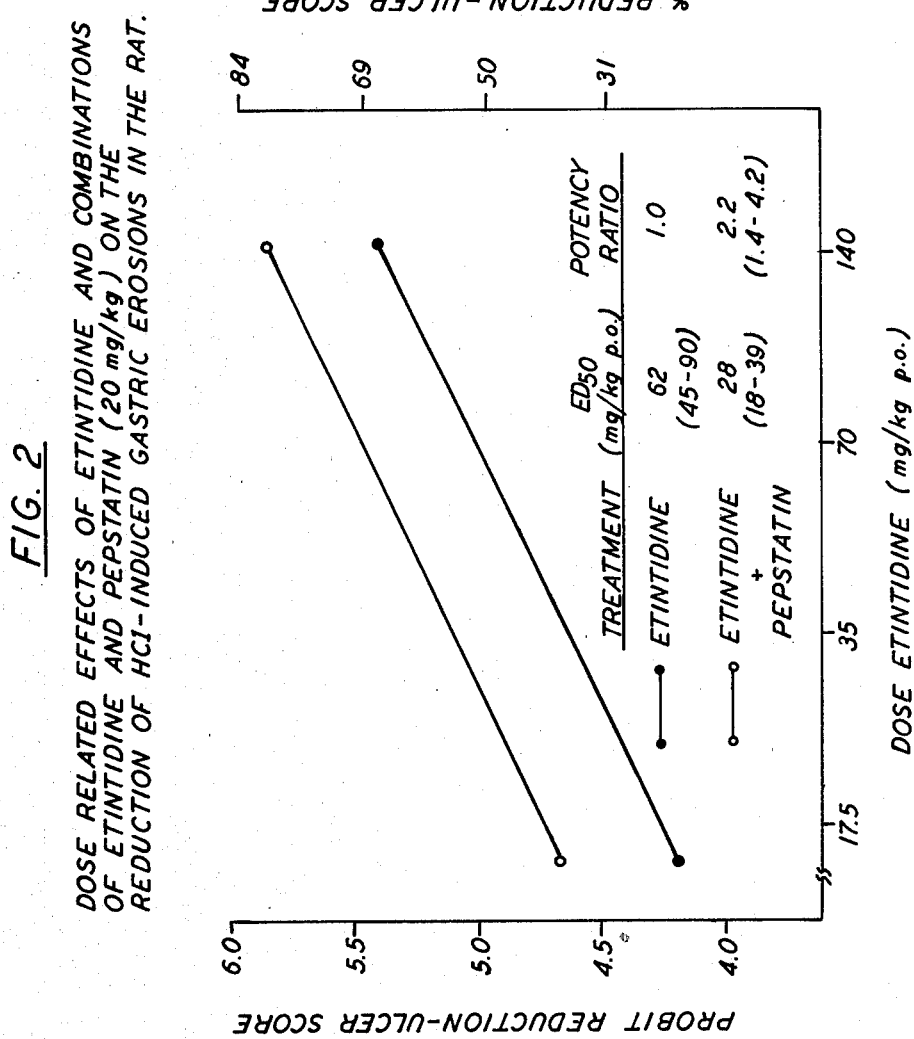

PHARMACEUTICAL METHODS AND COMPOSITIONS

SUMMARY OF THE INVENTION

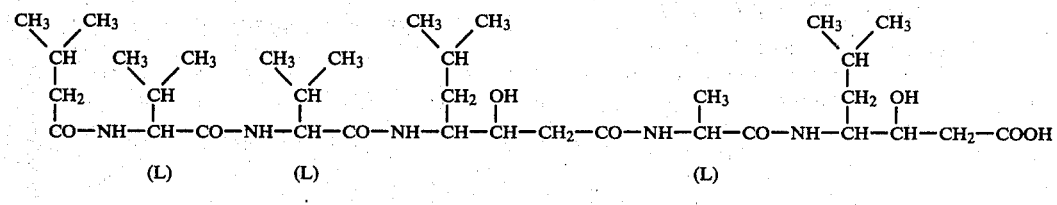

In the treatment of peptic ulcers in warm-blooded animals, the concomitant administration of the pepsin-complexing agent, pepstatin, and the histamine $H_2$-receptor antagonist, etintidine, provides enhanced antiulcer activity, reduces the amount of etintidine necessary for effective treatment and thereby reduces the side effect liability of the etintidine. This invention relates to the method of treating peptic ulcers in warm-blooded animals by the concomitant administration of pepstatin and etintidine, and to pharmaceutical compositions containing these two entities.

BACKGROUND OF THE INVENTION

The precise cause of peptic ulceration in man is unknown although gastric acid is considered to be one of the essential factors in the etiology of this disease. It recently was discovered that gastric acid secretion is mediated, at least in part, by histamine $H_2$-receptors located on parietal cells in the gastric mucosa and that gastric acid output induced by all secretagogues could be antagonized by specific antagonists of these receptors [Black, J. W. et al., Nature, 236, 385–390 (1972); Brimblecombe, R. W. et al., J. Int. Med. Res., 3, 86–92 (1975)]. The first successful commercial histamine $H_2$-receptor antagonist, cimetidine, is now in widespread use as an antiulcer agent. Etintidine (BL-5641) is a new histamine $H_2$-receptor antagonist which is about twice as potent as cimetidine [Cavanagh, R. L. et al., Fed. Proc., 39, 768 (1980)].

The role of the proteolytic enzyme, pepsin, in the etiology of ulceration is not completely understood. Pepsin has been shown to play a major role in the development of experimentally induced ulcers in animals, but this may be due to lesion enlargement by means of pepsin digestion of necrotic tissue rather than by causing the initial damage. It is also possible that pepsin is entirely responsible for the erosions and that the acid produces pain and retards healing.

DESCRIPTION OF THE PRIOR ART (1) U.S. Pat. No. 4,112,234 discloses, inter alia, etintidine (BL-5641), which is the histamine $H_2$-receptor antagonist having the structure

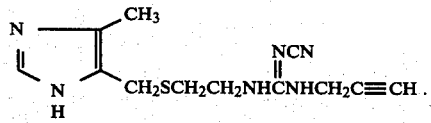

(2) Myers, W. M. and Peterson, W. L., in Clinical Research, 28, 30A (1980), describe clinical tests showing that etintidine effectively antagonizes meal stimulated gastric acid secretion in patients with inactive duodenal ulcers.

(3) Umezawa, H. et al., in J. Antibiotics, 23, 259–262 (1970), disclose the pentapeptide, pepstatin, which has the structure and which is a specific complexing agent for the enzyme pepsin. Pepstatin was found to prevent the formation of stomach ulcers in the pylorus ligated (Shay) rat.

(4) Bonnevie, O. et al., in Gut, 20, 624–628 (1979), report the results of a double-blind randomized clinical trial of pepstatin versus placebo in patients having duodenal ulcers. Pepstatin was administered in 100 mg doses, given seven times a day, this dosage being sufficient to inhibit the peptic activity of gastric juice for 18 hours a day. They found no significant difference between pepstatin and placebo in the healing or symptomatology of duodenal ulcer.

(5) Svendsen, L. B. et al., in Scand. J. Gastroent., 14, 929–932 (1979), report the results of a double-blind randomized clinical trial of pepstatin versus placebo in patients having gastric ulcer. Pepstatin was administered in 100 mg doses seven times a day. They were not able to detect any influence of pepstatin either on the healing or on the symptomatology of gastric ulcer.

(6) Strauss, R. J. et al., in Surg. Forum, 28, 361–363 (1977), disclose that, in stress ulceration tests in rats, two or more days of pretreatment with either cimetidine or carbenoxolone significantly decreased ulcer formation. When the two agents were given together, significant ulcer reduction was found after only one-half day of predosing. Carbenoxolone is not an antisecretory or anti-pepsin agent, but acts by stimulating gastric mucus synthesis.

(7) Dajani, E. Z. et al., in J. Pharmacol. Exp. Ther., 210, 373–377 (1979), disclose that, in stress ulceration tests in rats, a combination of cimetidine and propantheline bromide produced synergistic antiulcer activity and that a combination of cimetidine and thiopropazate hydrochloride produced additive antiulcer activity. Propantheline bromide (an anticholinergic agent) and thiopropazate hydrochloride (a tranquilizer) each act by inhibiting gastric secretion.

(8) British Medical Journal, 95–96 (1980) reviews the results obtained in a large number of studies with various new antiulcer agents. With regard to pepsin antagonists, it states:

"The results of using pepsin antagonists have been uniformly disappointing. Amylopectin showed no significant benefit in patients with duodenal ulcer, and sucralfate showed none in those with gastric ulcer. Even pepstatin, the most potent in-vitro and in-vivo pepsin antagonist, was ineffective in a formal controlled trial in healing duodenal ulcer and in preventing recurrent bleeding in patients admitted with haematemesis and melaena."

(9) U.S. Pat. No. 4,101,650 discloses long-acting pepstatin floating minicapsules comprising center particles of sodium bicarbonate coated with a water-soluble film-coating agent, which are further coated with pepstatin and a water-soluble film coating agent. Because of the release of carbon dioxide in gastric juice, these minicapsules float in the stomach and provide pepsin suppression for 3-5 hours as compared with about 1 hour for plain pepstatin.

COMPLETE DISCLOSURE

This invention relates to antiulcer therapy. In one aspect it relates to a pharmaceutical composition comprising a mixture of the histamine $H_2$-receptor antagonist, etintidine, or a pharmaceutically acceptable acid addition salt thereof, and the pepsin-complexing agent, pepstatin. In another aspect this invention relates to the method of treating peptic ulcers in a warm-blooded animal in need of such treatment which comprises concomitantly administering to said animal a peptic activity-inhibiting amount of pepstatin and an effective antiulcerogenic amount of etintidine, or a pharmaceutically acceptable acid addition salt thereof. In still another aspect this invention relates to the improvement in the treatment of peptic ulcers in a warm-blooded animal by the administration to said animal of an effective antiulcerogenic amount of etintidine, or a pharmaceutically acceptable acid addition salt thereof, which improvement comprises reducing the amount of etintidine, or salt thereof, necessary for effective treatment by concomitantly administering to said animal a peptic activity-inhibiting amount of pepstatin.

Etintidine is a relatively nontoxic substance, as demonstrated by pharmacological studies in animals. These studies showed a toxicity profile substantially the same as that of the commercial $H_2$-antagonist cimetidine. Although widespread human usage of cimetidine has demonstrated it to be a relatively safe drug with a low incidence of side-effects, it would of course be desirable to even further reduce such side-effects. Etintidine has been shown to be from about 1.5 to about 2 times as potent as cimetidine in various animal studies. Based on the potency difference, the dosage of etintidine alone would be from about one-half to about two-thirds that of cimetidine thus reducing the expected incidence of side-effects. The usual dosage of cimetidine is 300 mg, given four times a day, while the usual dosage of etintidine is 150–200 mg, given four times a day. It was an object of the present invention to further reduce the necessary dosage of etintidine by the concomitant administration of a peptic activity-inhibitory amount of pepstatin. As will be shown below, such concomitant administration provides a two-fold increase in potency compared with the administration of an equal amount of etintidine alone, thus permitting a further two-fold reduction in the dosage of etintidine.

Pepstatin has also been shown by pharmacological studies in animals to be a relatively nontoxic substance; its $LD_{50}$ exceeded 3000 mg/kg in all animal species studied [Svendsen, L. B. et al., Scand. J. Gastroent., 11, 459–463 (1976)]. It is essentially unabsorbed upon oral administration; no side effects were observed in human patients with ulcer dyspepsia receiving daily oral doses of 700 mg of pepstatin for up to three months [Svendsen, L. B. et al. (1976) supra]. Pepstatin does not inhibit the production of pepsin but inhibits peptic activity by forming a 1:1 pepsin-pepstatin complex which is devoid of proteolytic activity.

In patients with ulcer dyspepsia, it has been demonstrated that pepstatin inhibits gastric peptic activity, but has no effect on the gastric acidity [Svendsen, L. B. et al., Scan. J. Gastroent., 11, 459–463 (1976)]. In contrast, the histamine $H_2$-receptor antagonist cimetidine has been shown to antagonize both basal and stimulated gastric acid secretion in normal volunteers [Burland, W. L. et al., Brit. J. Clin. Pharmacol., 2, 481–486 (1975)] and in patients with duodenal ulcer [Longstreth, G. F. et al., New England J. Med., 294, 801–804 (1976)], but its effect on pepsin secretion is less marked [Binder, H. J. and Donaldson Jr., R. M., Gastroenterology, 74, 371–375 (1978)]. The results of those studies indicate that pepstatin and cimetidine act by different mechanisms. The inhibitory effect of etintidine on gastric acid secretion is also significantly greater than on pepsin activity, and in this respect its pharmacological profile is similar to that of cimetidine.

In the tests described below, gastric erosions produced in rats by the oral instillation of 1.0 ml of 0.75 N HCl were compared with those in rats which had been pretreated with etintidine or with etintidine and pepstatin.

EXPERIMENTAL METHODS

A modification of the method of Robert et al., [Gastroenterology, 77, 433–443 (1979)] was employed to produce gastric erosions. Adult male, Long Evans rats weighing 280–300 g (Blue Spruce Farms, Alton, New York) were used. The animals were individually caged and food and water were removed 24 and 18 hours, respectively, prior to testing. On the following day, etintidine was administered orally to the animals 30 minutes before 1.0 ml of 0.75 N HCl was instilled into the stomach by gavage. Animals treated with the combination of etintidine and pepstatin received etintidine 30 minutes before, and a fixed amount of pepstatin (20 mg/kg po) 10 minutes before, the hydrochloric acid was administered. Previous studies in our laboratories had shown that this dose of pepstatin (20 mg/kg po) completely inhibited pepsin activity and antagonized ulcer formation in the 18 hour pylorus ligated rat. One hour after receiving the HCl solution, the animals were sacrificed with an intraperitoneal injection of 0.2 ml of T-61®, a euthanasia solution (National Laboratories Corp.).

The stomachs were removed from the animals, cut along the greater curvature, opened, rinsed with saline and pinned out flat in a standard position for macroscopic examination and scoring of erosions. The stomachs were photographed with a Polaroid® Close Up camera (Polaroid Corporation) and scoring was determined from the photographs. For scoring purposes, only those erosions with a minimum length of 1 mm were considered. The severity of gastric ulceration was defined for each animal as the sum of the maximum continuous lengths (in mm) of the erosions satisfying the above criteria. Percent inhibition of lesion formation was defined as $$\frac{(mm\ erosion,\ vehicle\ control) - (mm\ erosion,\ test\ agent)}{(mm\ erosion,\ vehicle\ control)} \times 100$$

Data were analyzed using the t-test for unpaired data and $ED_{50}$ values were calculated from dose response data using probit analysis [Finney, Probit Analysis, 3rd ed., University Press, Cambridge, England (1971)].

Etintidine (synthesized by the Medicinal Chemistry Research Department of Bristol Laboratories, division of Bristol-Myers Company) was dissolved in one equivalent of HCl and the pH adjusted to 5.5 with NaOH. A suspension of pepstatin (Banyu Pharmaceutical Co. Ltd.) in water was made by homogenizing the compound with a few drops of Tween-80 ® (Atlas Chemical Industries). Both compounds were administered orally by gavage in a volume of 2 ml/kg.

TEST RESULTS

The instillation of HCl to untreated rats caused extensive gastric erosions consisting of elongated bands 1–10 mm long by 1–3 mm wide. These erosions were located primarily in the corpus (portion of the stomach which secretes acid and pepsin), while the antrum was not as severely affected and no lesions were observed in the forestomach (the non-secretory portion). These findings are similar to those reported by Robert et al., in their initial description of this procedure.

Pretreatment of the rats with a 17.5, 35, 70 or 140 mg/kg dose of etintidine prior to instillation of the HCl decreased the formation of gastric erosions in a dose-related manner. Pretreatment of rats with the above amounts of etintidine plus 20 mg/kg of pepstatin significantly enhanced the inhibitory effect of etintidine at etintidine levels of 17.5, 35 and 70 mg/kg. No further enhancement of the inhibitory effect over that of etintidine alone occurred when pepstatin and 140 mg/kg of etintidine were used for pretreatment. FIG. 1 shows, in graphic form, the percent of reduction in gastric erosions over that of the control rats (no pretreatment) which was obtained at each of the dosage levels of etintidine alone and etintidine plus pepstatin.

When the data shown in FIG. 1 were analyzed by regression analysis, it was shown that the response to etintidine was linear and that the addition of pepstatin shifted the dose response to the left in a parallel manner. These data are shown in FIG. 2. It may be seen from FIG. 2 that the $ED_{50}$ values for etintidine alone and the etintidine-pepstatin combination were found to be 62 and 28 mg/kg, respectively, thus showing that the etintidine-pepstatin combination had more than twice the potency of etintidine alone.

Pepstatin is only poorly absorbed following oral administration as animal studies have shown that more than 90 percent of the compound is excreted in the feces within 72 hours. Therefore, the inhibition of proteolytic activity following oral administration of pepstatin is due primarily to a local effect of this compound.

In order to obtain the maximum benefit of the present invention, it is desirable that the dosage of pepstatin be such that there is substantially complete inhibition of gastric pepsin activity for as long a period of the day as practical. When pepstatin was administered to ulcer patients in 100 mg doses seven times a day (with meals, two hours after meals and at bedtime), pepsin activity was inhibited for 18 hours a day.

In one preferred embodiment of this invention, pepstatin is administered in dosages of about 100 mg seven times a day. In another preferred embodiment of this invention, pepstatin is administered in dosages of about 175 mg four times a day. In a more preferred embodiment of this invention the pepstatin is administered in the form of floating minicapsules as described in U.S. Pat. No. 4,101,650. The pepstatin floating minicapsules provide pepsin suppression for about 3–5 times as long as plain pepstatin and, in this form, may be administered, for example, four times a day in a dosage of floating minicapsules containing about 100 mg of pepstatin.

The dosage of etintidine used in this invention is from about 50 to about 150 mg, given three or four times a day (e.g. with meals and at bedtime). The most preferred dosage of etintidine in this invention is from about 75 to about 100 mg, given four times a day.

It will be appreciated by those skilled in the art that, to obtain the benefits of the present invention, it is not necessary to physically combine the etintidine and pepstatin in a single unitary dosage form. Not only may the two active ingredients be taken separately, but they may even be given by different routes of administration. Although pepstatin provides its effects by local action in the stomach and must be given orally, etintidine may be given orally or parenterally. For convenience, however, it usually is preferred to administer the etintidine orally.

The present invention provides a method for the treatment of peptic ulcers in a warm-blooded animal in need of such treatment which comprises concomitantly administering to said animal a peptic activity-inhibiting amount of pepstatin and an effective antiulcerogenic amount of etintidine, or a pharmaceutically acceptable acid addition salt thereof. In man, the preferred dosage of etintidine is from about 50 to about 150 mg (and most preferably from about 75 to about 100 mg), given three or four times (and most preferably four times) a day. The preferred dosage of pepstatin in man is from about 100 mg when administered about seven times a day, to about 175 mg when administered about four times a day. However, in a more preferred embodiment of this invention, when the pepstatin is in the form of pepstatin floating minicapsules, the preferred dosage is that amount of minicapsules containing about 100 mg of pepstatin, administered about four times a day.

The present invention also provides an improvement in the method of treatment of peptic ulcers in a warm-blooded animal by administering to said animal an effective antiulcerogenic amount of etintidine or a pharmaceutically acceptable acid addition salt thereof, which improvement comprises reducing the amount of etintidine necessary for effective treatment by concomitantly administering a peptic activity-inhibiting amount of pepstatin. The preferred dosage of pepstatin and of pepstatin floating minicapsules in man is as described in the preceding paragraph.

There is also provided by the present invention a pharmaceutical composition useful in the treatment of peptic ulcers, in unit dosage form, which comprises a peptic activity-inhibiting amount of pepstatin and an effective antiulcerogenic amount of etintidine, or a pharmaceutically acceptable acid addition salt thereof, and a pharmaceutically acceptable carrier. In a preferred embodiment the unitary dosage form contains from about 50 to about 150 mg (and most preferably from about 75 to about 100 mg) of etintidine and from about 100 to about 175 mg of pepstatin.

As used herein, reference to a pharmaceutically acceptable acid addition salt of etintidine means the mono- or di-salt of etintidine with a nontoxic pharmaceutically acceptable organic or inorganic acid. Such acids are well known and include hydrochloric, hydrobromic, sulfuric, sulfamic, phosphoric, nitric, maleic, fumaric, succinic, oxalic, benzoic, methanesulfonic, ethanedisulfonic, benzenesulfonic, acetic, propionic, tartaric, citric, camphorsulfonic, and the like. The salts are made by methods known in the art.

In practicing the present invention, a wide variety of pharmaceutical forms may be employed for the administration of the etintidine and pepstatin, or the pharmaceutical composition containing both entities. Thus, if a solid carrier is used, the preparations may be tableted, placed in a hard gelatin capsule in powder or pellet form, or in the form of a troche or lozenge. If a liquid carrier is used, the preparations may be in the form of a soft gelatin capsule, syrup, emulsion, aqueous or nonaqueous suspension or, in the case of etintidine, a sterile solution or suspension for injection. These pharmaceutical dosage forms are prepared by conventional techniques.

We claim:

1. A method for the treatment of peptic ulcers in a warm-blooded animal in need of such treatment which comprises concomitantly administering to said animal a peptic activity-inhibiting amount of pepstatin and an effective antiulcerogenic amount of etintidine, or a pharmaceutically acceptable acid addition salt thereof.

2. The method of claim 1 wherein the dosage of pepstatin is from about 100 to about 175 mg and wherein the dosage of etintidine is from about 50 to about 150 mg.

3. The method of claim 1 or 2 wherein the pepstatin is administered in the form of pepstatin floating minicapsules.

4. The method for the treatment of peptic ulcers in a warm-blooded animal in need of such treatment which comprises concomitantly administering to said animal about 175 mg of pepstatin and from about 75 to about 100 mg of etintidine.

5. The method for the treatment of peptic ulcers in a warm-blooded animal in need of such treatment which comprises concomitantly administering to said animal about 100 mg of pepstatin in the form of pepstatin floating minicapsules and from about 75 to about 100 mg of etintidine.

6. The method of claim 4 or 5 wherein the pepstatin and etintidine are administered four times a day.

7. In the method of treatment of peptic ulcers in a warm-blooded animal by administering to said animal an effective antiulcerogenic amount of etintidine or a pharmaceutically acceptable acid addition salt thereof, the improvement which comprises reducing the amount of etintidine necessary for effective treatment by concomitantly administering a peptic activity-inhibiting amount of pepstatin.

8. The improved method of claim 7 wherein the dosage of pepstatin is from about 100 to about 175 mg.

9. The improved method of claim 7 or 8 wherein the pepstatin is administered in the form of pepstatin floating minicapsules.

10. In the method of treatment of peptic ulcers in a warm-blooded animal by administering to said animal an effective antiulcerogenic amount of etintidine or a pharmaceutically acceptable acid addition salt thereof, the improvement which comprises reducing the amount of etintidine necessary for effective treatment by concomitantly administering about 175 mg of pepstatin.

11. In the method of treatment of peptic ulcers in a warm-blooded animal by administering to said animal an effective antiulcerogenic amount of etintidine or a pharmaceutically acceptable acid addition salt thereof, the improvement which comprises reducing the amount of etintidine necessary for effective treatment by concomitantly administering about 100 mg of pepstatin in the form of pepstatin floating minicapsules.

12. The improved method of claim 10 or 11 wherein the pepstatin and etintidine are administered four times a day.

13. A pharmaceutical composition useful in the treatment of peptic ulcers, in unit dosage form, which comprises a peptic activity-inhibiting amount of pepstatin and an effective antiulcerogenic amount of etintidine, or a pharmaceutically acceptable acid addition salt thereof, and a pharmaceutically acceptable carrier.

14. The pharmaceutical composition of claim 13 which comprises from about 50 to about 150 mg of etintidine and from about 100 to about 175 mg of pepstatin.

15. The pharmaceutical composition of claim 13 or 14 wherein the pepstatin is in the form of pepstatin floating minicapsules.

16. A pharmaceutical composition useful in the treatment of peptic ulcers, in unit dosage form, which comprises from about 75 to about 100 mg of etintidine or a pharmaceutically acceptable acid addition salt thereof, and about 175 mg of pepstatin, in a pharmaceutically acceptable carrier.

17. A pharmaceutical composition useful in the treatment of peptic ulcers, in unit dosage form, which comprises from about 75 to about 100 mg of etintidine or a pharmaceutically acceptable acid addition salt thereof, and about 100 mg of pepstatin in the form of pepstatin floating minicapsules, in a pharmaceutically acceptable carrier.

* * * * *